(12) United States Patent
Green et al.

(10) Patent No.: US 6,171,486 B1
(45) Date of Patent: *Jan. 9, 2001

(54) LIQUID CHROMATOGRAPHY COLUMN

(75) Inventors: Jeffrey R. Green, San Francisco, CA (US); Jeffrey A. Kaster, Charlottesville, VA (US); Victor R. Lancaster, Los Gatos, CA (US); Peter J. Leavesley, Charlottesville, VA (US); Gary L. McNeil, Cambridge; Thomas C. Ransohoff, Lexington, both of MA (US); Peter C. Van Davelaar, Maiden, VA (US)

(73) Assignee: Dyax Corporation, Cambridge, MA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/190,418

(22) Filed: Nov. 12, 1998

Related U.S. Application Data

(63) Continuation-in-part of application No. 08/970,287, filed on Nov. 14, 1997, now abandoned, and a continuation-in-part of application No. 08/970,286, filed on Nov. 14, 1997, now abandoned.

(51) Int. Cl.[7] .................................................. B01D 15/08
(52) U.S. Cl. ........................................ 210/198.2; 210/656
(58) Field of Search ................................ 210/198.2, 232, 210/238, 282, 450, 635, 656; 96/101, 105, 106

(56) References Cited

U.S. PATENT DOCUMENTS

| | | | |
|---|---|---|---|
| 2,998,036 | 8/1961 | Strasheim et al. | 141/72 |
| 3,300,849 | 1/1967 | Wiseman | 29/124 |
| 3,398,512 | 8/1968 | Perkins, Jr. et al. | 55/386 |
| 3,440,864 | 4/1969 | Blume | 73/61.1 |
| 3,511,377 | 5/1970 | Hrdina | 210/198 |

(List continued on next page.)

OTHER PUBLICATIONS

Merriam–Webster's Collegiate Dictionary Tenth Edition 1998, p. 210, Springfield Massachuetts.*
BioSepra, "Hyperdiffusion Chromatography", Apr. 1995, pp. 6, 7, and 13.*
BioSepro, "HyperDiffusion Chromatography", pp. 6, 7, 13, Apr. 1995.
Pharmacia Biotech—Process Products '95, "High Purity in Industrial Chromatography" Undated pp. 1–5.
POROS 50 EP and OH Perfusion Chromatography, "Operating Instructions" Undated pp. 1 & 2.
3M Emphaze—Biosuport Medium, "Introduction to 3M Emphaze Biosupport Medium", 1992, pp. 1–3.
EM Separations Technology, "Tentacle Ion Exchange Chromatography Handbook", pp. 1 and 4, Undated.
Biotage (Separations at Any Scale), "Lightning Fast Flash Chromatography Cartridges" 1995. pp. 1 & 2.

(List continued on next page.)

Primary Examiner—Ernest G. Therkorn
(74) Attorney, Agent, or Firm—Fish & Richardson P.C.

(57) ABSTRACT

A chromatography cartridge assembly includes a cartridge and first and second end caps. A wall of the cartridge defines a chamber for containing chromatography media. The end caps define inlet and outlet passages, respectively, for flow of process fluid. The first end cap defines flow distributor passages for distributing process fluid across a cross-sectional area of the chamber, and the second end cap defines flow collector passages for collecting process fluid from across a cross-sectional area of the chamber. A clamp is circumferentially located about the cartridge wall for applying a radial load through the wall to the first end cap to fix the first end cap in a desired position.

25 Claims, 12 Drawing Sheets

U.S. PATENT DOCUMENTS

| | | | |
|---|---|---|---|
| 3,615,235 | | 10/1971 | Hrdina .................................... 25/253 |
| 3,682,315 | * | 8/1972 | Haller ................................ 210/198.2 |
| 3,935,884 | | 2/1976 | Hazelton .............................. 141/180 |
| 3,966,609 | | 6/1976 | Godbille et al. ..................... 210/198 |
| 4,250,035 | * | 2/1981 | McDonald ......................... 210/198.2 |
| 4,280,905 | | 7/1981 | Gunkel et al. ..................... 210/198.2 |
| 4,354,932 | * | 10/1982 | McNeil .............................. 210/198.2 |
| 4,361,482 | | 11/1982 | Teetz et al. ....................... 210/198.2 |
| 4,375,743 | * | 3/1983 | Sullivan ................................ 53/470 |
| 4,384,957 | | 5/1983 | Crowder, III et al. .............. 210/656 |
| 4,451,365 | | 5/1984 | Sattler et al. ..................... 210/198.2 |
| 4,483,374 | | 11/1984 | Siemion .................................. 141/9 |
| 4,549,584 | | 10/1985 | Morin et al. ........................... 141/73 |
| 4,557,830 | * | 12/1985 | Onitsuka ........................... 210/198.2 |
| 4,565,632 | | 1/1986 | Hatch et al. ........................ 210/656 |
| 4,582,608 | | 4/1986 | Ritacco ................................ 210/656 |
| 4,597,866 | | 7/1986 | Couillard .......................... 210/198.2 |
| 4,627,918 | | 12/1986 | Saxena ................................ 210/656 |
| 4,636,315 | * | 1/1987 | Allen ................................. 210/198.2 |
| 4,636,316 | | 1/1987 | Harris et al. ...................... 210/198.2 |
| 4,670,141 | | 6/1987 | Shackelford et al. ............. 210/198.2 |
| 4,732,687 | | 3/1988 | Muller et al. ..................... 210/198.2 |
| 4,737,292 | | 4/1988 | Ritacco et al. ....................... 210/656 |
| 4,755,293 | | 7/1988 | Sakamoto et al. ................ 210/198.2 |
| 4,769,141 | | 9/1988 | Couillard .......................... 210/198.2 |
| 4,865,728 | | 9/1989 | Larsson ............................ 210/198.2 |
| 4,865,729 | | 9/1989 | Saxena et al. .................... 210/198.2 |
| 4,882,047 | * | 11/1989 | Shalon .............................. 210/198.2 |
| 4,890,753 | * | 1/1990 | Duryee et al. .......................... 53/527 |
| 4,891,133 | * | 1/1990 | Colvin, Jr. ........................ 210/198.2 |
| 4,927,531 | | 5/1990 | Sakamoto et al. ................ 210/198.2 |
| 4,968,421 | | 11/1990 | Spacek et al. .................... 210/198.2 |
| 5,021,162 | | 6/1991 | Sakamoto et al. .................. 210/635 |
| 5,069,069 | | 12/1991 | Miyagishi et al. ................ 210/198.2 |
| 5,137,628 | | 8/1992 | Hart et al. ......................... 210/198.2 |
| 5,141,635 | | 8/1992 | LePlang et al. .................. 210/198.2 |
| 5,167,810 | * | 12/1992 | Vassarotti ......................... 210/198.2 |
| 5,192,433 | * | 3/1993 | Shalon .............................. 210/198.2 |
| 5,238,556 | * | 8/1993 | Shirkhan .......................... 210/198.2 |
| 5,282,973 | * | 2/1994 | Mann ................................ 210/198.2 |
| 5,324,426 | | 6/1994 | Joseph et al. ..................... 210/198.2 |
| 5,338,448 | | 8/1994 | Gjerde .............................. 210/198.2 |
| 5,366,621 | * | 11/1994 | Bidell ............................... 210/198.2 |
| 5,378,361 | | 1/1995 | Baeckstrum ...................... 210/198.2 |
| 5,423,982 | | 6/1995 | Jungbauer et al. ............... 210/198.2 |
| 5,482,628 | | 1/1996 | Schick .............................. 210/198.2 |
| 5,601,708 | * | 2/1997 | Leavesley ........................ 210/198.2 |
| 5,651,885 | * | 7/1997 | Schick .............................. 210/198.2 |
| 5,651,886 | * | 7/1997 | Hoffman .......................... 210/198.2 |
| 5,671,928 | | 9/1997 | Lanyi et al. .......................... 277/207 |
| 5,693,223 | * | 12/1997 | Yamada ............................ 210/198.2 |
| 5,714,074 | | 2/1998 | Karlsson et al. ..................... 210/656 |
| 5,714,677 | * | 2/1998 | Parsy et al. ........................... 96/105 |
| 5,736,036 | * | 4/1998 | Upchurch ......................... 210/198.2 |

OTHER PUBLICATIONS

Snyder, Introduction to Modern Liquid Chromatography, John Wiley & Sons, New York, 1979, pp. 624–625.

Skea, "Process High Performance Liquid Chromatography", High Performance Liquid Chromatography, vol. 98, Chapter 12, 489–500.

Search Report for PCT/US98/24058 Dated Jan. 26, 1999.

EM Separations Technology—Superformance Pilot and Production Glass Columns, "Chromatography Columns" pp. 68–71, 1995.

* cited by examiner

LIQUID CHROMATOGRAPHY COLUMN

This application is a continuation-in-part of application U.S. Ser. No. 08/970,287, filed Nov. 14, 1997 now abandoned, and application, U.S. Ser. No. 08/970,286, filed Nov. 14, 1997, now abandoned.

BACKGROUND OF THE INVENTION

This invention relates to liquid chromatography columns.

Cartridges for use in liquid chromatography are known in which a flow distributor and a flow collector are located in the vicinity of the end caps of the cartridge to distribute and collect the process fluid.

SUMMARY OF THE INVENTION

The invention features, in general, a chromatography cartridge assembly including a cartridge and a first end cap. A wall of the cartridge defines a chamber for containing chromatography media. The first end cap is positioned within a first end cap receiving opening of the cartridge. The first end cap defining a passage for flow of process fluid. A clamp is circumferentially located about the cartridge wall for applying a radial load through the wall to the end cap to fix the end cap in a desired position.

In preferred embodiments, a second end cap is positioned within a second end cap receiving opening of the cartridge. The second end cap defines a passage for flow of process fluid. A clamp is circumferentially located about the cartridge wall for applying a radial load to the second end cap to fix the second end cap in a desired position.

The first end cap includes flow distributor passages for distributing process fluid across a cross-sectional area of the chamber, and the second end cap includes flow collector passages for collecting process fluid from across a cross-sectional area of the chamber.

The inner surface of the wall has a constant diameter. Alternatively, the inner surface of the wall defines a section of constant inner diameter for slidably receiving the first end cap, and a circumferential groove for receiving the second end cap. Alternatively, the second unitary end cap is integral with the cartridge.

The end caps each include a sieve for retaining the chromatography media in the chamber. The sieve includes a fine mesh and a course mesh.

Flexible seals are located between the end caps and the wall of the cartridge. The first and second end caps each include a connector for attachment to an inlet conduit and an outlet conduit, respectively.

A support clamp holds the cartridge. The cartridge includes a flexible wall configured to radially compress the chromatography media. The chromatography media is a hydrophilic material. The chromatography media has an operating pressure rating greater than about 3 bar. The chromatography media has a particle size in the range of about 15–200 microns.

According to another aspect of the invention, a chromatography apparatus includes a cartridge assembly and a compression module surrounding the cartridge assembly. The compression module defines a pressure chamber for containing a pressurized fluid. The pressurized fluid acts to move a flexible wall of the cartridge.

According to another aspect of the invention, a method of revitalizing a packed column having trapped air includes providing a chromatography cartridge including a flexible wall defining a chamber. The flexible wall forms a movable diaphragm for compressing chromatography media located within the chamber. Compression is applied to the chromatography media to minimize the volume of trapped air.

In preferred embodiments, the compression is radial compression.

According to another aspect of the invention, a method of sealing a flexible-walled tube includes placing a sealing member within the tube, positioning a first conical member around the outside of the tube and axially aligned with the sealing member, and positioning a second conical member around the outside of the tube and in contact with the first conical member. An axial load is applied to the second conical member, whereby the axial load on the second conical member acts to radially compress the first conical member. The radial compression causes permanent deformation of the first conical member and the adjacent wall of the tube to seal the sealing member within the tube. The seal is maintained upon removal of the axial load.

In preferred embodiments, the sealing member is an end cap defining an inlet passage for flow of process fluid and flow distributor passages for distributing process fluid across a cross-sectional area of the tube.

According to another aspect of the invention, a clamping mechanism for sealing a sealing member within a tube includes a first conical member for placement around the outside of the tube, a second conical member for placement around the outside of the tube and in contact with the first conical member, and a load applicator for applying an axial load to the second conical member. The axial load on the second conical member acts to radially compress the first conical member. The radial compression causes permanent deformation of the first conical member and the adjacent wall of the tube to seal the sealing member within the tube.

According to another aspect of the invention, a chromatography column includes a column having a flexible-wall. The column contains chromatography media. An end cap is positioned within the column and defining an inlet passage for flow of process fluid and flow distributor passages for distributing process fluid across a cross-sectional area of the column. A clamp is located around an outside of the column for sealing the end cap within the column.

In preferred embodiments, the clamp radially compresses the flexible wall to seal the end cap within the column. The clamp is a conical member.

Advantages include a cartridge which can be dynamically compressed and used as a stand alone device. The cartridge is disposable and provides convenience over glass columns which the user packs themselves. The cartridge seals are static and thus easier to clean between runs than the dynamic seals in a glass column.

Additional advantages include liquid chromatography of biomolecule process fluids under pressures above 3 bar. The materials used in the chromatography apparatus prevent biomolecule precipitation and non-specific adsorption. The cartridge within a module system permits changeout of wetted components and reuse of the module for different biomolecules without cross-contamination.

Other advantages and features of the invention will ba apparent from the following description of a preferred embodiment thereof and from the claims.

BRIEF DESCRIPTION OF THE DRAWINGS

The drawings will be described first.

Drawings

DESCRIPTION OF THE PREFERRED EMBODIMENT

Figure 1:
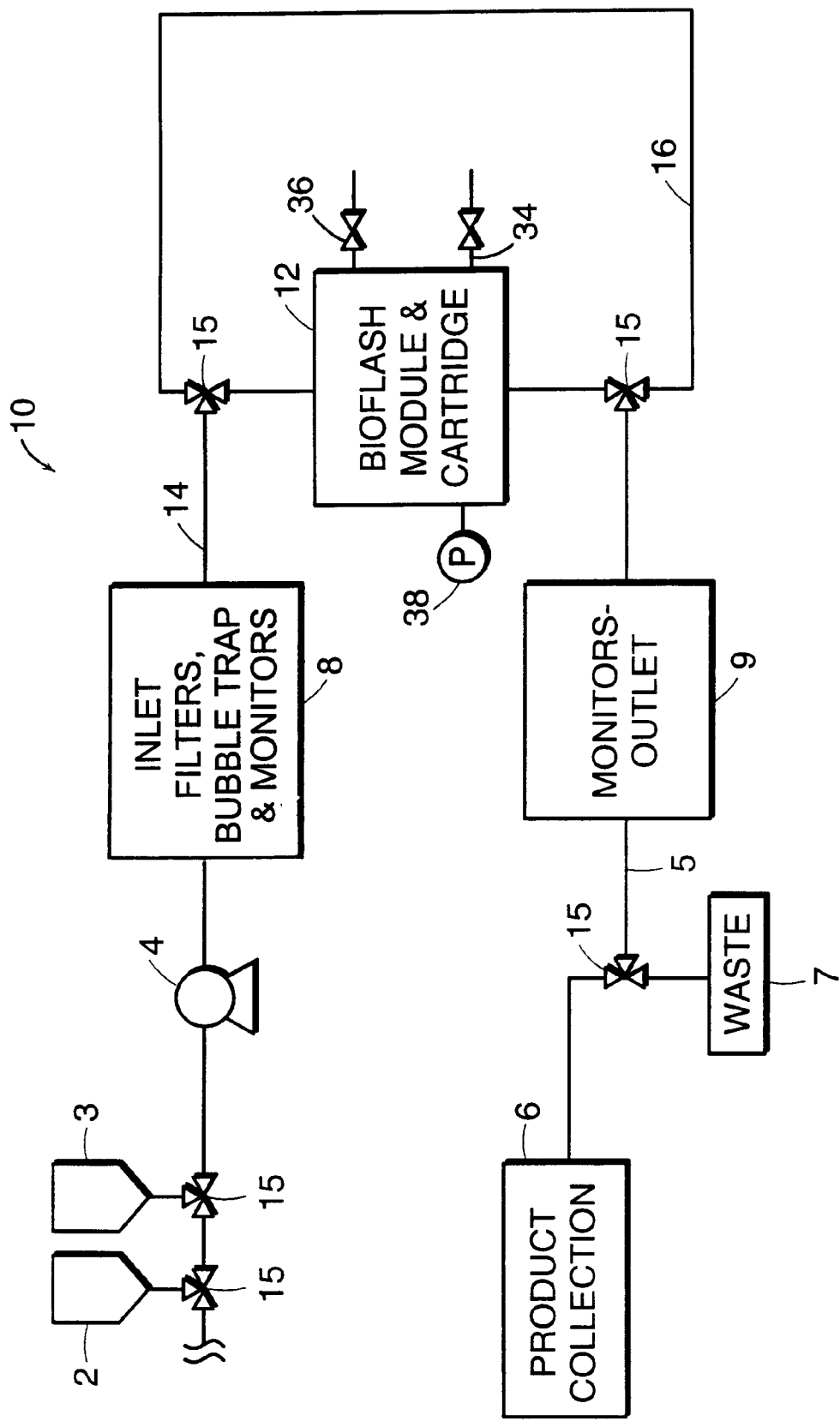
FIG. 1 is a schematic of a chromatography apparatus according to the invention.

Referring to FIG. 1, an apparatus 10 is shown for performing chromatography separation of biomolecules, e.g., proteins, oligosaccharides, large DNA molecules, and viral particles, in an aqueous based solvent. The term biomolecules is not meant to include synthetic organic chemicals, small linear peptides, or chiral compounds. Apparatus 10 includes a chromatography assembly 12 and inlet solution tank 2, load tank 3, and system pump 4 for delivering process fluid under pressure along a process inlet path 14 to chromatography assembly 12. An outlet line 5 leads from chromatography assembly 12 to a product collection vessel 6 and a waste receptacle 7. A water filter, bubble trap and monitor 8 (monitoring, e.g., pressure, conductivity, and pH) are located along the process fluid inlet path 14. A monitor 9 monitoring, e.g., pressure, conductivity, pH, and UV absorbance, is located along outlet line 5. A column bypass 16 permits the system to be cleaned while bypassing the chromatography assembly. Valves 15 control the flow of the process fluid.

Figure 2:
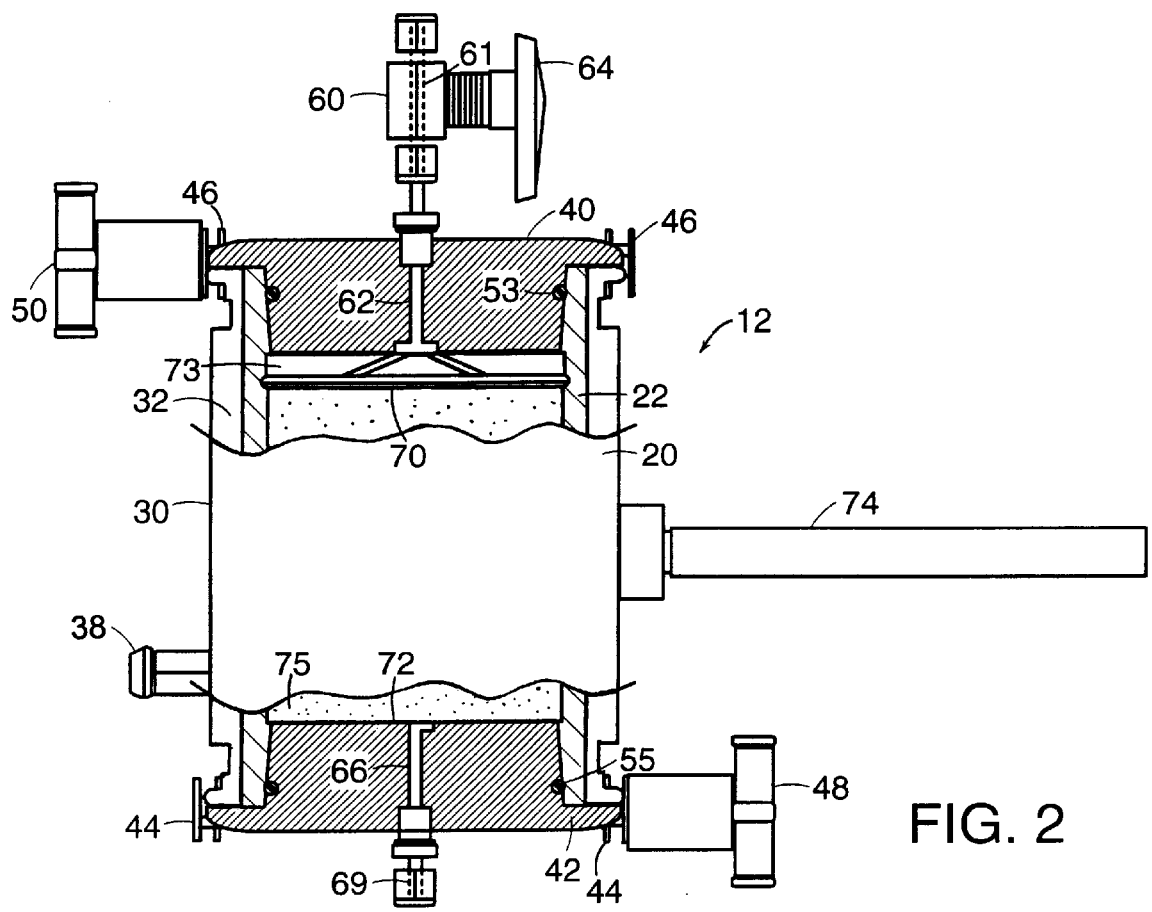
FIG. 2 is a partially cut-away, cross-sectional side view of the pressure module of the invention.
Figure 2A:
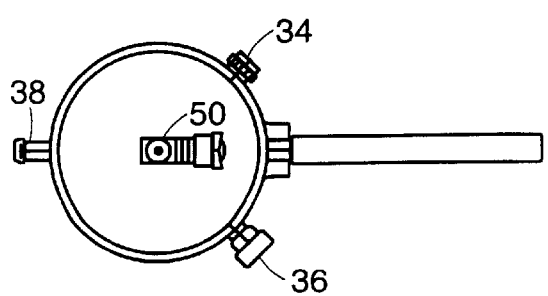
FIG. 2A is a top view of the pressure module of FIG. 2.
Figure 2B:
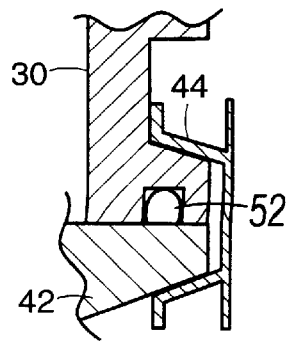
FIG. 2B is an enlarged view of the clamping region of the pressure module of FIG. 2.

Referring to FIGS. 2–2B, chromatography assembly 12 includes a compression module 20 and a cartridge assembly 22. Compression module 20 includes a housing 30, formed from, e.g., stainless steel or aluminum, defining a cylindrical region 32 for containing fluid for applying radial compression to cartridge assembly 22. A compressible or incompressible fluid can be used to apply radial compression pressure to cartridge assembly 22.

The application of radial compression to a chromatography cartridge is described in U.S. Pat. No. 4,250,035 to McDonald, hereby incorporated by reference. Briefly, in a liquid chromatography column, a stationary phase such as silica is packed in a cartridge having a flexible wall. By exerting radial pressure on the cartridge, packing bed voids are avoided and wall channeling effects are overcome. The packing efficiency of the column is increased and is more reproducible, and greater uniformity can be achieved in column performance both among packed columns of the same kind and during the useful life of a given packed column.

Referring to FIGS. 1 and 2A, housing 30 includes a fluid inlet 34, a relief valve 36 for purging pressure within cylindrical region 32, and a pressure indicator 38. Radial compression pressure applied to cartridge assembly 22 is controlled by a pressure regulator or a pump (not shown) which delivers fluid to fluid inlet 34; solvent flow rate through the cartridge assembly is controlled by pump 4. A mounting arm 74 connected to housing 30 can be used to mount chromatography assembly 12 to a laboratory stand.

Removable end caps 40, 42 retain cartridge assembly 22 in place within compression module 20. Referring particularly to FIG. 2B, end cap 42 is mounted to housing 30 with a band clamp 44 (end cap 40 is similarly mounted to housing 30 with a band clamp 46). Clamp tightening knobs 48, 50 are used to tighten band clamps 44, 46 respectively. At higher pressures, the knobs can be replaced with bolts to meet code requirements. As shown in FIG. 2B, each end cap 40, 42 is sealed against housing 30 with an o-ring 52 to prevent leakage of compression fluid from region 32. As shown in FIG. 2, end caps 40, 42 are sealed against cartridge assembly 22 by o-rings 53, 55, respectively, which separate compression fluid from process fluid.

An inlet connector 60 defines a channel 61 leading to an inlet passage 62 defined by end cap 40 for flow of process fluid into cartridge assembly 22. Control knob 64 is used to open and close channel 61. An outlet passage 66 defined by end cap 42 leads to an outlet connector 68 defining a channel 69 for flow of process fluid out of cartridge assembly 22. Inlet and outlet passages 62 and 66 include o-ring seals 70, 72, respectively, for sealing the passages against cartridge assembly 22. End caps 40, 42 are preferably made from a hydrophilic material, e.g., stainless steel, to prevent precipitation of biomolecules on the surfaces of passages 62, 66. Seals 70 and 72 prevent flow of process fluid along the interface 73 between end cap 40 and cartridge 22 and the interface 75 between end cap 42 and cartridge 22 thus minimizing the exposure of the process fluid to dead spaces and crevices in which microbial growth and attachment could occur.

Figure 3:
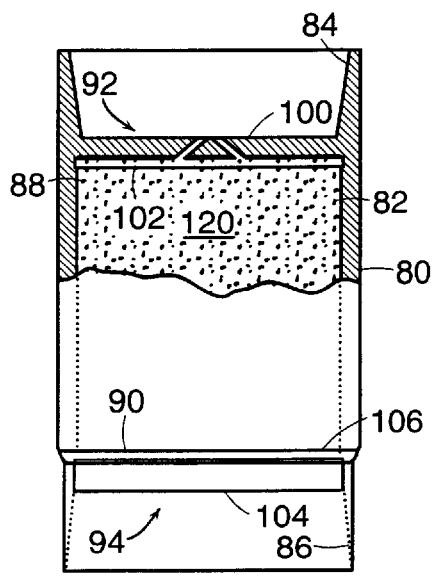
FIG. 3 is a partially cut-away, cross-sectional side view of a cartridge assembly of the invention.

Referring to FIG. 3, cartridge assembly 22 has a flexible wall 80 partially defining a media chamber 82. Flexible wall 80 further defines end cap receiving openings 84, 86. The upper and lower ends 88, 90 of media chamber 82 are defined by flow assemblies 92, 94 respectively. Upper flow assembly 92 includes a flow distributor 100 and a sieve 102, e.g., a mesh or frit. A mesh is preferred over a frit due to its smaller surface area which limits biomolecule adhesion. Lower flow assembly 94 includes a flow collector 104 and a sieve 106. The flow distributor 100, flow collector 104, and sieves 102, 106 are preferably made from hydrophilic materials having surface energies greater than about 36 dyn/cm, e.g., polyamide, polyethyleneterephthalate, polyvinylidene chloride, polymethylmethacrylate, and polystyrene, to limit biomolecule binding to the surfaces and clogging of the sieves. Materials having surface energies less than 36 dyn/ cm are not suitable for separating biomolecules because the biomolecules adhere to the material thus clogging the cartridge assembly.

Figure 4A:
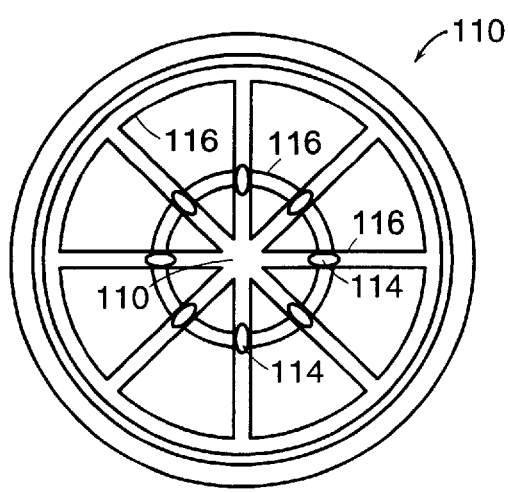
FIG. 4A is a sectional view of the distributor of FIG. 4, taken along lines 4A—4A.
Figure 4:
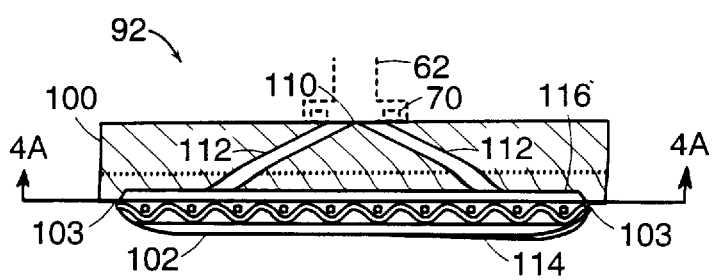
FIG. 4 is a cross-sectional side view of a distributor and mesh of the invention.

Referring to FIGS. 4 and 4a, sieve 102 is welded to flow distributor 100 along outer periphery 103 of flow distributor 100. Welding along periphery 103 permits process fluid to flow through sieve 102 but not around it, and prevents media particles from leaking around sieve 102 into flow distributor 100. Sieve 106 is similarly welded to flow collector 104.

The process fluid path is from inlet passage 62 to an inlet 110 of flow distributor 100. Multiple flow channels 112, 8 channels being shown in the illustrated embodiment, run from inlet 110 to outlets 114. Outlets 114 connect flow channels 112 to a network of channels 116 which distribute the process fluid. Sieve 102 preferably has a pore size of about 10–20 micron to allow passage of process fluid while preventing passage of chromatography media. Flow collector 104 and sieve 106 are identical to flow distributor 100 and sieve 102. Flow collector 104 and sieve 106 are mounted such that process fluid first passes through sieve 106 and then through the network of channels 116 to finally be collected at inlet 110.

Figure 5:
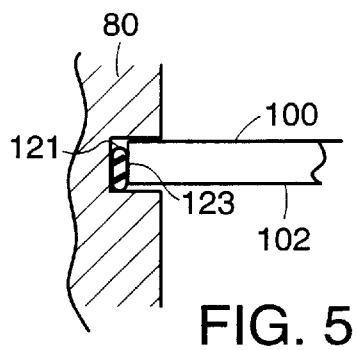
FIG. 5 is an enlarged schematic view of a sealing scheme of the invention.
Figure 6:
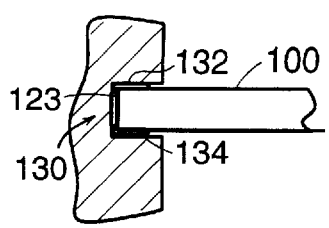
FIG. 6 is an enlarged schematic view of an additional sealing scheme of the invention.

An alternative or additional sealing scheme which further limits voids and dead spaces in which process fluid can be trapped is shown in FIG. 5. Here, an o-ring 121 positioned between flow distributor 100 and cartridge wall 80 prevents flow of process fluid around edge 123 of the flow distributor and into crevices where the process fluid can be trapped. Similarly, an o-ring can be positioned between flow collector 104 and cartridge wall 80. Additionally, referring to FIG. 6, the flow distributor and/or flow collector can be welded at 130 along edge 123 and side portions 132, 134 to the cartridge wall, thereby creating a low dead volume seal.

Example operating pressure (process fluid flow pressure) ratings achievable with chromatography assembly 12 employing an aluminum compression module 20 are listed below. For an incompressible compression fluid, the operating pressure can be equal to the pressure rating of the pressure module. For a compressible compression fluid, the operating pressure is about 1 to 6 bar less than the pressure rating of the pressure module because the compression pressure applied to the cartridge is greater than the process fluid pressure to maintain the integrity of the cartridge. Higher pressure ratings are achievable depending upon tube thickness and by substituting stainless steel for aluminum.

| inner diameter of compression module 20 (mm) | pressure (bar) |
| --- | --- |
| 75 | 20–35 |
| 100 | 14–23 |
| 150 | 10–17 |
| 300 | 6–14 |
| 400 | 4–10 |

Referring again to FIG. 3, chromatography media 120 is contained within media chamber 82 by upper and lower sieves 102, 106. Due to recent advances in materials technology leading to the development of the new hydrophilic and rigid support matrices having high pressure ratings, the high pressure ratings achievable with chromatography assembly 12 and the hydrophilic materials used in the critical components of cartridge assembly 22 enable fast, high resolution biomolecule separation. Suitable matrices for chromatography media 120 include Emphaze™, available from Pierce; POROS®, available from PerSeptive Biosystems; HyperD™, available from BioSepra; Source™, available from Pharmacia Biotech, Sweden; Toyopearl®, available from TosoHaas; Fractogel®, available from E. Merck, Germany, Macro-Prep®, available from BioRad; Bakerbond®, available from Baker Mallinckrodt; Sepharose®, available from Pharmacia Biotech; and Amberchrom, available from TosoHaas. The media listed above have particle sizes in the range of 15–100 microns, though media can be used having larger particle sizes, up to at least about 200 microns. Another suitable matrix for chromatography media 120 is a continuous bed matrix, e.g., the UNO Continuous Bed Matrix, available from BioRad. The pressure ratings and available functionalities of each material are listed below.

| Matrix | Pressure Rating (bar) | Available Functionalities |
| --- | --- | --- |
| POROS ® | 100 | ion exchange hydrophobic interaction affinity |
| HyperD ™ | 200 | ion exchanqe affinity |
| Emphaze ™ | 7 | affinity |
| Fractogel ® | 10 | ion exchange hydrophobic interaction affinity |
| Toyopearl ® | at least 7 | ion exchange hydrophobic interaction affinity |
| Source ™ | 50 | ion exchange hydrophobic interaction |
| Macro-Prep ® | 55 | ion exchange |
| Bakerbond ® | 70–140 | ion exchange hydrophobic interaction |
| Sepharose ® | 3 | ion exchange hydrophobic interaction affinity |
| Amberchrom | Not Available | reverse phase |
| UNO Matrix | 48 | ion exchange |

Sepharose has a pressure rating of about 3 bar. All the other media have pressure ratings above 3 bar, above 5 bar, and some have pressure ratings about 50 bar, with one having a rating greater than 150 bar.

The radial pressure applied to the chromatography media should be at least equal to the flow pressure of the process fluid to maintain the integrity of the column. When using a compressible compression fluid, the radial pressure applied is in the range of about 1 to 6 bar over the operating pressure.

The surfaces of chromatography assembly 12 exposed to process fluid include cartridge 22, flow distributor 100, flow collector 104, sieves 102, 106, and end caps 40, 42. As discussed previously, the flow distributor, flow collector and sieves are formed from hydrophilic materials to prevent biomolecule precipitation and non-specific adsorption. The sieves are preferably polymeric as opposed to stainless steel due to the stainless steel's poorer chemical resistance and susceptibility to chloride attack. Because the surface area of cartridge 22 exposed to the process fluid is much less than that of the flow distributor, flow collector, and sieves, cartridge 22 can be formed from a less hydrophilic material, e.g., polyethylene having a surface energy of 35.7 dyn/cm (linear PE) and 35.3 dyn/cm (branched PE). Though to minimize biomolecule precipitation and non-specific adsorption on the cartridge, preferably a more hydrophilic material is also used for cartridge 22. End caps 40, 42 are preferably stainless steel.

Seals 53, 55, 70, 72 insure that compression module 20 remains free of contamination from process fluid during use. The components of cartridge assembly 12 with wetted surfaces can be changed while the same compression module 20 can be used with a new sample without cross-contamination.

It is understood that separate inserts can be employed to define passages 62, 66 such that end caps 40, 42 are not exposed to process fluid and only the inserts need be removed and exchanged or cleaned between sample runs.

It has been found that radial compression can revitalize a packed column. Trapped air in the media causes bed cracking and loss of chromatographic efficiency. By subjecting the column to radial compression, the volume of air is minimized thus minimizing the effects of air entrapment such that there is little or no decrease in performance of the column.

Figure 7:
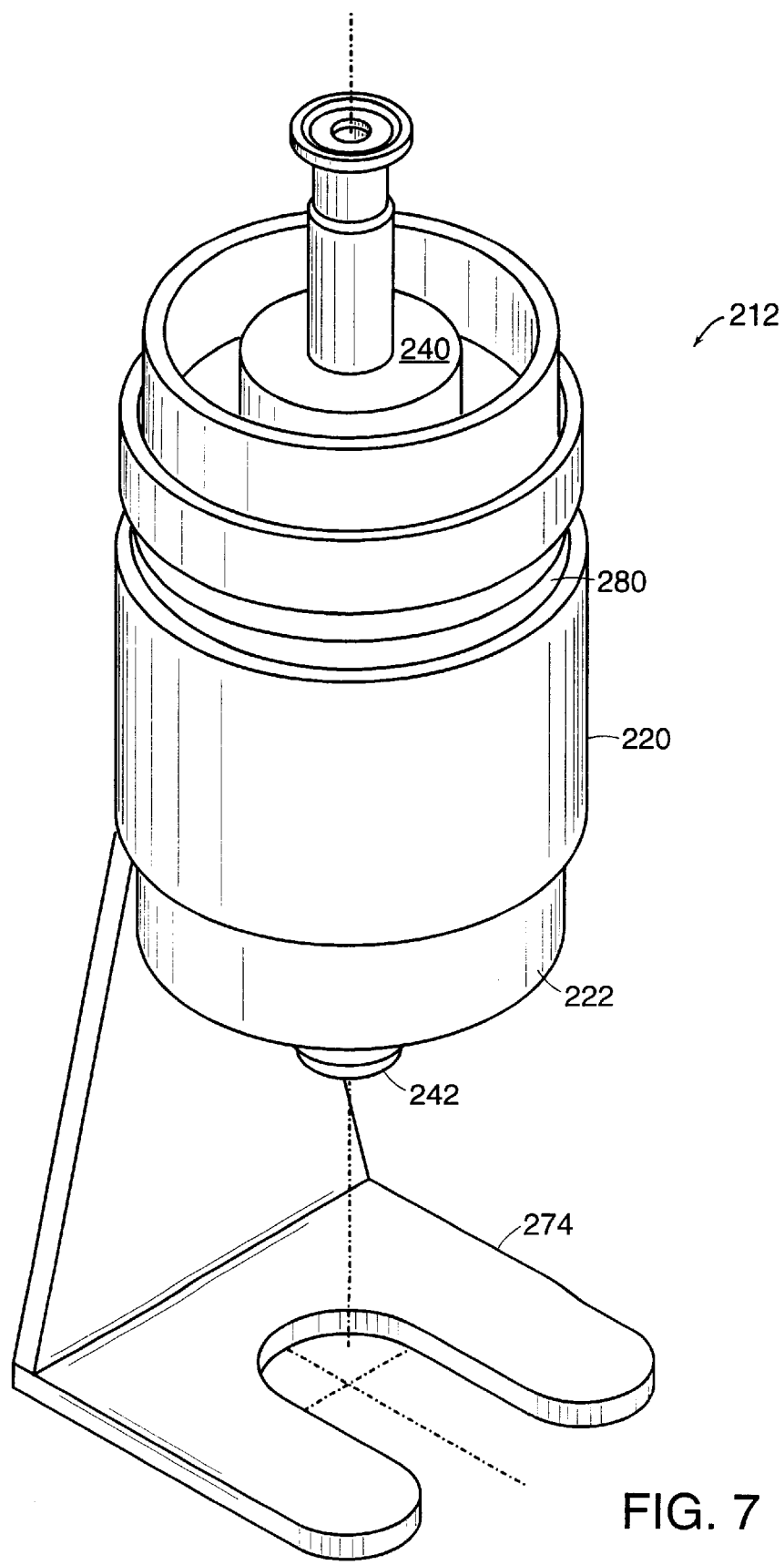
FIG. 7 is shows an additional embodiment of a chromatography assembly according to the invention.
Figure 8:
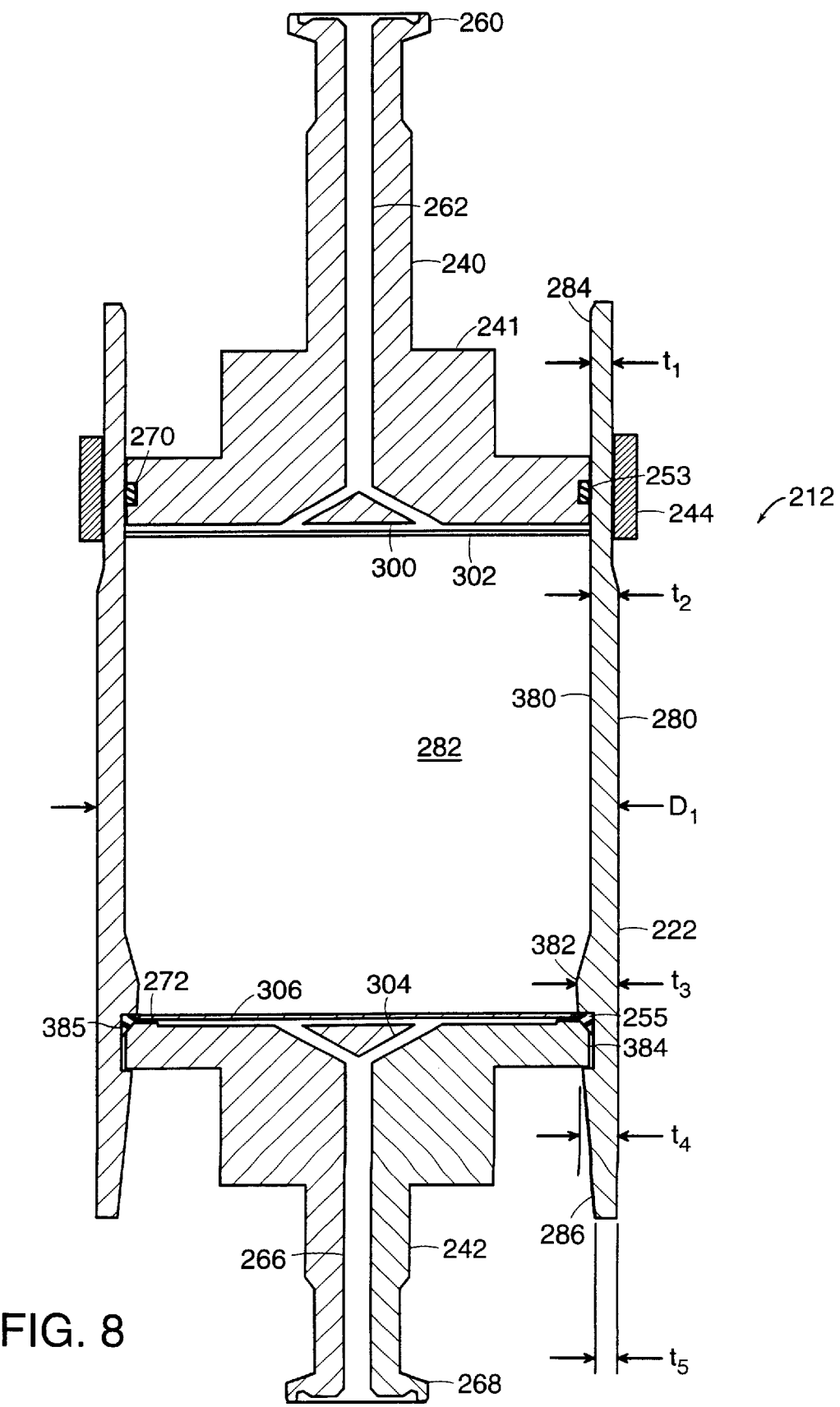
FIG. 8 is a cross-sectional side view of the cartridge and unitary end caps of the chromatography assembly of FIG. 7.

In another embodiment of the invention, referring to FIGS. 7 and 8, a chromatography assembly 212 includes a cartridge 222 and unitary end caps 240, 242. Cartridge 222 has a flexible wall 280 partially defining a media chamber 282. Flexible wall 280 further defines end cap receiving openings 284, 286. Cartridge 222 can be used alone or with a compression module, as described above. When used alone, cartridge 222 is supported by one or more mechanical support clamps 220. Clamps 220 can be connected to a stand 274, as described further below.

Cartridge assembly 212 can be formed of hydrophilic materials having surface energies greater than about 36 dyn/cm when used for separating biomolecules, as described above, and may be formed of other materials, e.g., polyethylene or stainless steel, when denaturation of biomolecules is not a concern.

Upper unitary end cap 240 includes an end cap body 241 defining a flow distributor section 300. Flow distributor section 300 is similar to flow distributor 100, described above with reference to FIGS. 4 and 4A, but in this embodiment the flow distributor is formed directly in the end cap body 241. A sieve 302 is welded to end cap body 241 along outer periphery 303 of end cap body 241 (see FIG. 9). Lower unitary end cap 242 similarly includes an integral flow collector 304 and a sieve 306.

Figure 9:
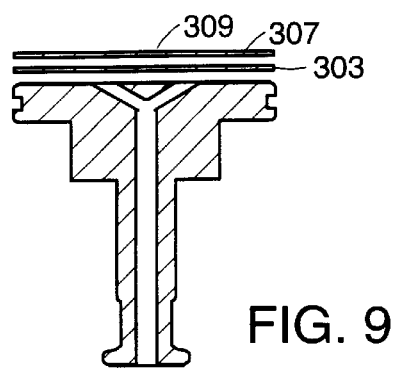
FIG. 9 is a cross-sectional, exploded side view of a unitary end cap of the chromatography assembly of FIG. 7.

Referring to FIG. 9, sieve 302 preferably includes a fine mesh 307 having a pore size of about 5–10 micron to allow passage of process fluid while preventing passage of chromatography media, and a coarse mesh 309 having a pore size of about 800 micron and provides support for the fine mesh. Flow collector 304 and sieve 306 are identical to flow distributor 300 and sieve 302.

Referring again to FIG. 8, cartridge wall 280 defines a first section 380 having a constant inner diameter, e.g., 3.187", and a second section 382 of decreased inner diameter, e.g., 3.01", resulting in an increase in the thickness of cartridge wall 280. Lower unitary end cap 242 is mechanically pressed into a circumferential channel 384, e.g., 0.11" deep, in wall 280. Alternatively, lower unitary end cap 242 can be formed integrally with cartridge wall 280, e.g., by molding the elements as a single unit, eliminating the need for o-ring 255, described below. The cartridge wall is dimensioned to provide flexibility so that the cartridge can be radially compressed and to provide a rigid wall when the cartridge is under ambient conditions. Cartridge wall 280 has dimensions of, e.g., a thickness $t_1$ of 0.1565", $t_2$ of 0.2065", $t_3$ of 0.295", $t_4$ of 0.25", and $t_5$ of 0.1625". Cartridge 222 has an outer diameter $D_1$ of, e.g., 3.60".

Each unitary end cap 240, 242 is sealed against wall 280 of cartridge 222 with an o-ring 253, 255, respectively to prevent leakage of process fluid between wall 280 and the end caps. Upper unitary end cap 240 defines a circumferential groove 270 in which o-ring 253 is located. O-ring 255 is located between wall 385 of channel 384 and a circumferential chamfer 272 defined by lower unitary end cap 242.

Upper unitary end cap 240 is slidably received within section 380 of cartridge 222 and is fixedly mounted to cartridge 222 with a band clamp 244, e.g., a blade draw latch type clamp or a J-style preformed hose clamp available from McMaster-Carr.

Upper unitary end cap 240 defines an inlet connector 260 and an inlet passage 262 for flow of process fluid into cartridge 222. Lower unitary end cap 242 defines an outlet connector 268 and an outlet passage 266 for flow of process fluid out of cartridge 222. The unitary end cap design minimizes the exposure of the process fluid to dead spaces and crevices in which microbial growth and attachment could occur.

Figures 10, 10A:
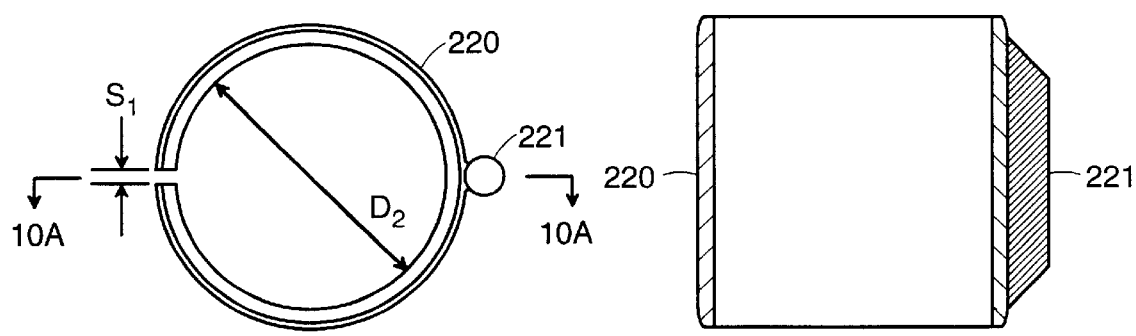
FIG. 10 is a top view of a support clamp of the chromatography assembly of FIG. 7.
FIG. 10A is a cross-sectional side view of the clamp of FIG. 10, taken along lines 10A—10A.

Referring to FIGS. 10 and 10A, clamp 220 has an inner diameter $D_2$ of, e.g., 3.650", and a space $S_1$ of e.g., 0.150" such that it holds cartridge 222. A mount 221 of clamp 220 permits the attachment of the clamp to support 274 as well as to any variety of supports to stabilize the cartridge during use and shipping. Clamp 220 can be secured about cartridge 222 with a closure (not shown) such as a screw or a single latch-type buckle.

Figure 11:
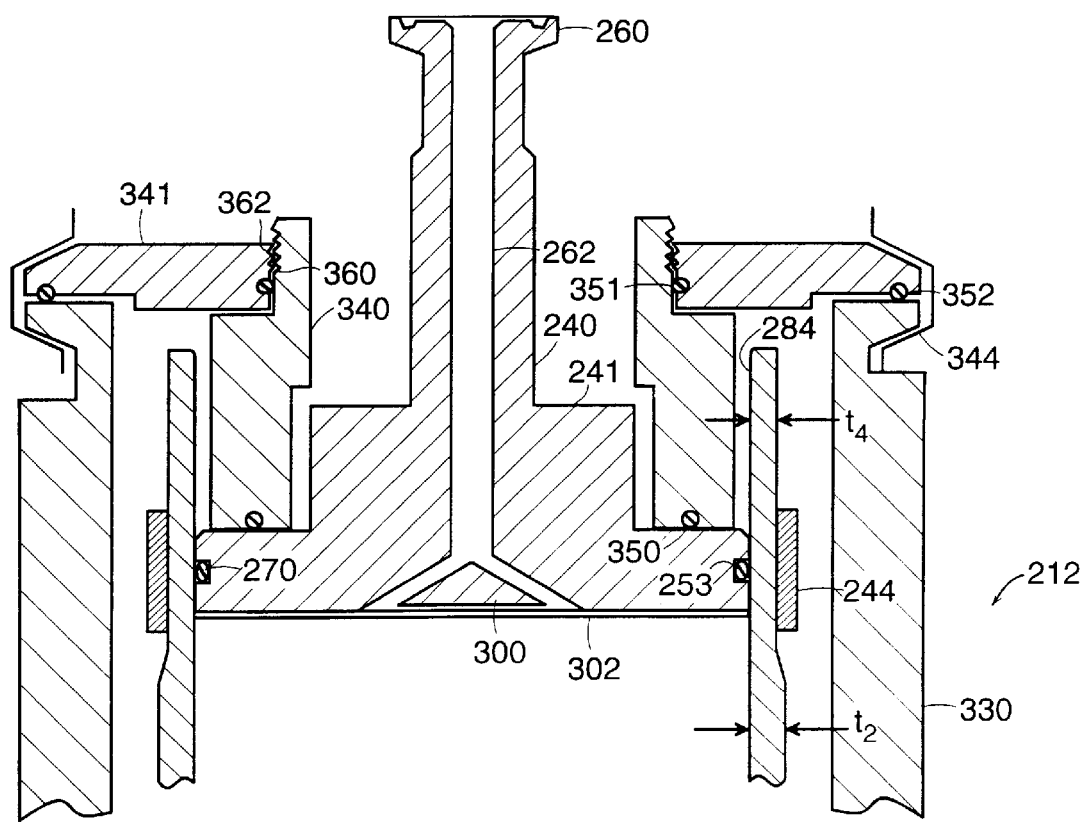
FIG. 11 is a cross-sectional side view of a section of a pressure module modified for use with chromatography assembly of FIG. 7.

Referring to FIG. 11, compression module 20 of FIG. 2 is shown modified to accommodate the unitary end caps of the cartridge assembly of FIG. 7. Removable end cap 40 of FIG. 2 have been replaced with a removable module sealing adapter 340 and a removable module end cap 341 (removable end cap 42 of FIG. 2 is similarly replaced with an identical removable module sealing adapter and end cap, not shown).

Adapter 340 and end cap 341 are mounted to module housing 330 with a band clamp 344. Sealing adapter 340 is sealed against unitary end cap 240, module end cap 341 is sealed against adapter 340, and module end cap 341 is sealed against housing 330, by o-rings 350, 351 and 352, respectively. Sealing adapter 340 and end cap 341 include mating threaded sections 360, 362 with o-ring 351 providing a sliding seal between sealing adapter 340 and end cap 341. The threaded connection between sealing adapter 340 and end cap 341 provides the degree of freedom necessary to adjust their relative positions dependent upon the final position of upper unitary end cap 240. Sealing adapter 340 and module end cap 341 are preferably formed from stainless steel.

Prior to filling cartridge 222 with chromatography media, lower unitary end cap 242 is positioned in cartridge 222. Cartridge 222 is then filled with chromatography media to a desired column height. Column packing may be performed as described in commonly owned U.S. patent application, U.S. Ser. No. 08/970,286, entitled CHROMATOGRAPHY MEDIA PACKING SYSTEM, filed Nov. 14, 1997, which is incorporated herein by reference. Upper unitary end cap 240 is then slid into cartridge 222 to rest against the chromatography media. The performance characteristics of the packed cartridge are then tested. If the column does not perform as desired, upper unitary end cap 240 can be removed and the column repacked. After the desired performance characteristics are obtained, upper unitary end cap 240 is held in place with band clamp 244.

Figure 12:
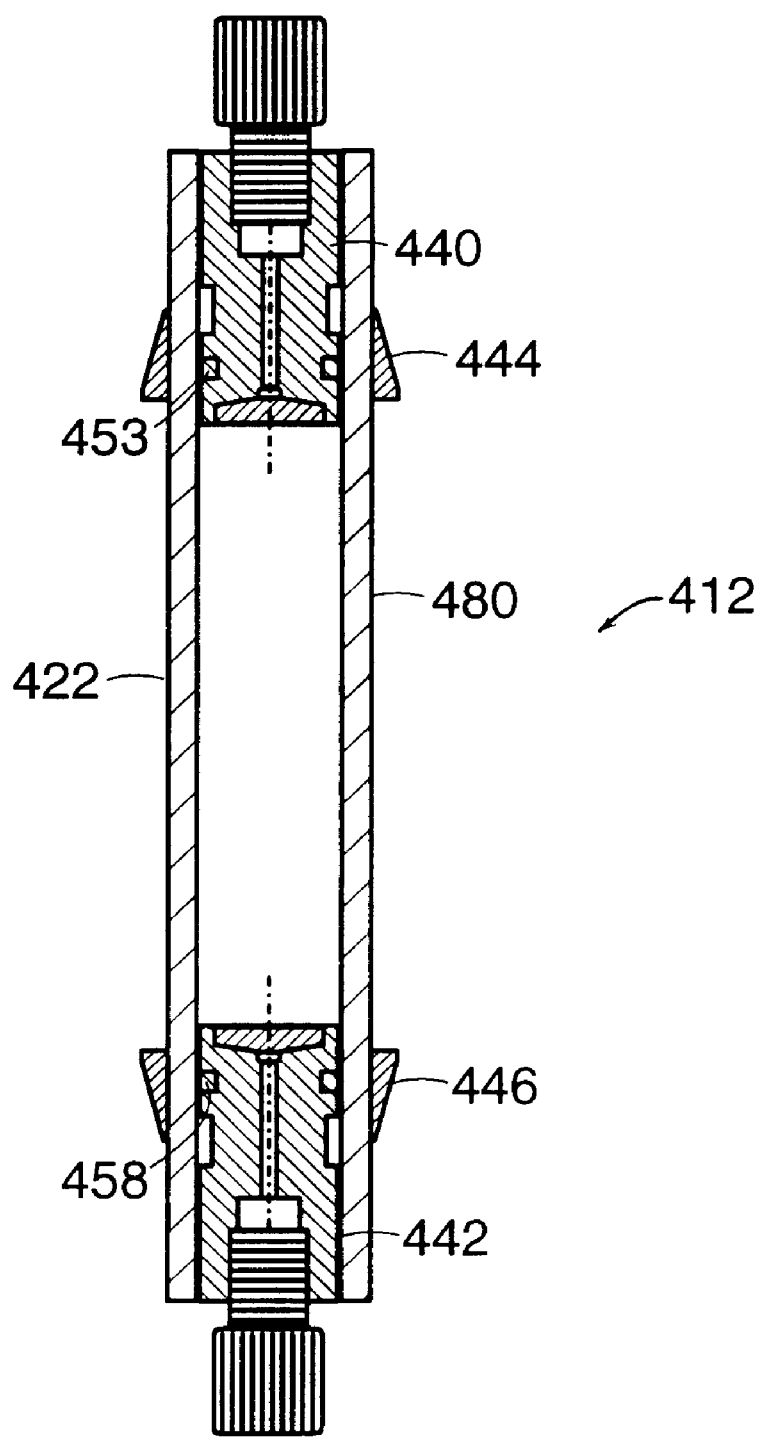
FIG. 12 is a cross-sectional side view of an additional embodiment of a chromatography cartridge.

An alternative method of fixing the end caps in place will now be described. Referring to FIG. 12, a chromatography assembly 412 includes a cartridge 422 and sealing members, e.g., unitary end caps 440, 442, fixed to cartridge 422 with clamps 444, 446, respectively. Unitary end caps 440, 442 are similar to unitary end caps 240, 242, described above, having an integral flow distributor and sieve (e.g., a mesh or frit), and integral flow collector and sieve (e.g., a mesh or frit), respectively.

Cartridge 422 has a flexible wall 480 with a constant inner diameter in the range of, e.g., about 0.472" to 16", an outer diameter in the range of, e.g., about 0.63" to 16.375", and a wall thickness in the range of, e.g., about 0.08 to 0.375". Cartridge 422 can be made from, e.g., polyproplyene, polyetheylene, nylon, or thin-walled (e.g., 0.03") stainless steel.

Unitary end caps 440, 442 are slidably received within cartridge 422 and fixed at desired locations within cartridge 422 with clamps 444, 446, respectively, as described below. Each unitary end cap 440, 442 is sealed against wall 480 of cartridge 422 with an o-ring 453, 455, respectively, to prevent leakage of process fluid between wall 480 and the end caps. Alternatively, lower unitary end cap 442 can be formed integrally with cartridge wall 480, e.g., by molding the elements as a single unit.

Prior to filling cartridge 422 with chromatography media, lower unitary end cap 442 is positioned in cartridge 422 and clamped in place with clamp 446, as described below. Cartridge 422 is then filled with chromatography media to a desired column height. The column is then packed, with upper unitary end cap 440 being slid into cartridge 422 to rest against the chromatography media. After the desired performance characteristics are obtained, upper unitary end cap 440 is fixed in place with clamp 444.

Figure 13B:
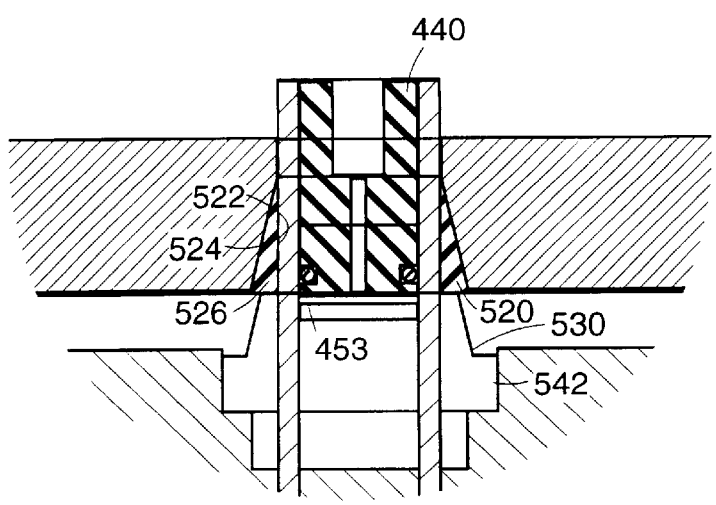
FIGS. 13a and 13b are cross-sectional side views of the chromatography cartridge of FIG. 12 mounted to a stand.
Figure 13A:
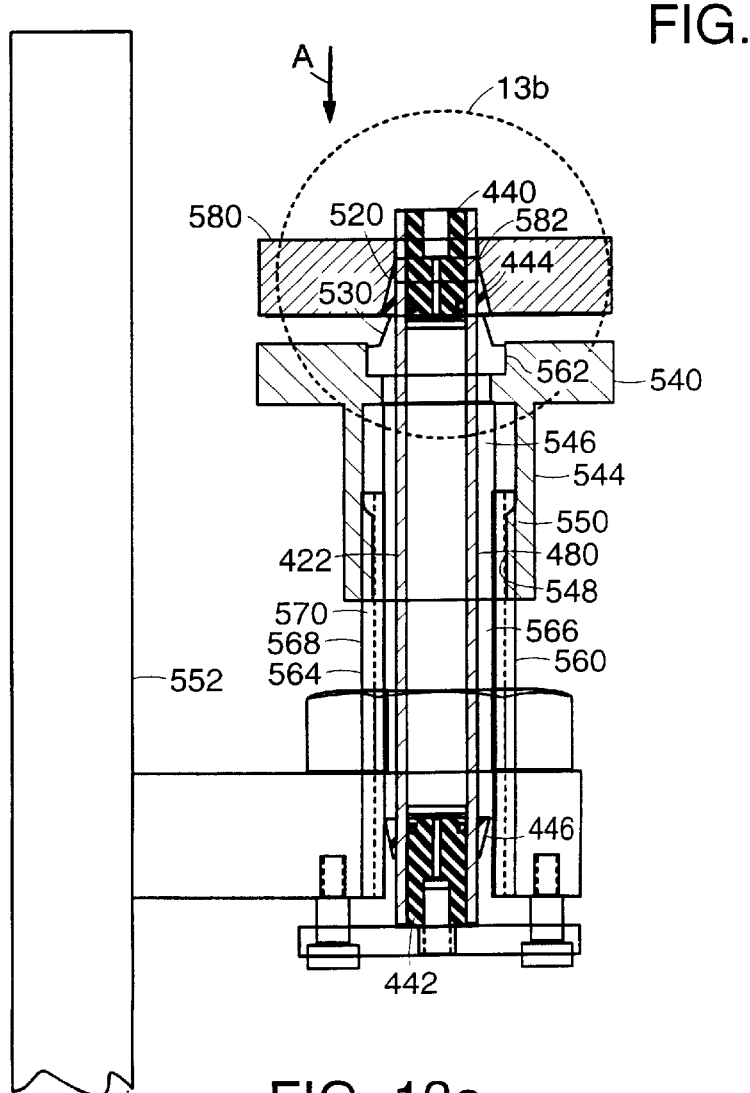

Referring to FIGS. 13a and 13b, lower clamp 446 is shown in position fixing lower end cap 442 within cartridge 422, and upper clamp 444 is shown prior to clamping of upper end cap 440. Clamp 444 (as well as clamp 446) is in the form of a ring 520 having a cylindrical inner wall 522 and a conical outer wall 524. To fix end cap 440 in place, ring 520 is slid over cartridge wall 480 and positioned in the vicinity of o-ring 453. An axial load, in the direction of arrow, A, is then applied to ring 520. Due to the conical shape of ring 520, the axial load is converted to an inward, radial compressive load in ring 520. The compressive load acts to permanently deform ring 520 and portions of cartridge wall 480 adjacent ring 520. This deformation of cartridge wall 480 acts to fix end cap 440 within cartridge 422.

A backup ring 530 axially supports and positions ring 520. Backup ring 530 presses against a larger end 526 of ring 520. Backup ring 530 is stronger than ring 520 to withstand the load applied to ring 520 without deforming. Backup ring 530 preferable includes two or more segments which permit backup ring 530 to be removed after use without the need to slide the backup ring to the end of cartridge 422, which may be obstructed by another compressed ring or other items.

Backup ring 530 is located within a counter-bore 542 of a support tube 540. Support tube 540 has a wall 544 defining a bore 546 through which cartridge 422 passes. An inner surface 548 of wall 544 is threaded at 550. Support tube 540 is attached to a stand 552 by a support arm 560. Support arm 560 has a wall 564 defining a bore 566 through which cartridge 422 passes. An outer surface 568 of wall 564 is threaded at 570. Rotation of support tube 540 relative to support arm 560 permits axial adjustment of the position of backup ring 530 along cartridge 422.

To apply the axial load to ring 520, a compressing ring 580 having an inner conical wall 582 complementary to conical wall 524 of ring 520 is positioned over ring 520 opposite backup ring 530. Compressing ring 580 is stronger than ring 520 to withstand the load applied to ring 520 without deforming. Compressing ring 580 can also be composed of two or more segments, if necessary.

The angle of inner conical wall 582 of compressing ring 580 should match the angle of conical wall 524 of ring 520 if a flat compression against wall 480 is desired. A 14 degree cone angle (28 degree included angle) has been found to be suitable. Larger angles require more axial force to apply the necessary compressive force. Smaller angles can make it difficult to separate compressing ring 580 from ring 520 after compressing ring 520. A smaller angle also requires longer axial motion of compressing ring 580 to achieve the desired deformation of ring 520. The best angle for a given application depends on several factors including the ring material (which should be malleable), surface finish, plating, lubrication, and available forces.

If an angled compression contact is desired, the angle of inner conical wall 582 can be set at a different angle than that of conical wall 524. Alternatively, cylindrical wall 522 can be conical instead of cylindrical to create an angled compression contact.

Figure 14B:
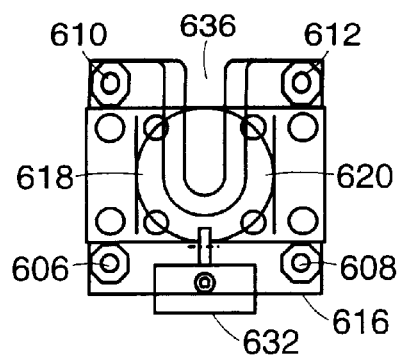
FIGS. 14a and 14b are side and top views, respectively, of a load applicator for clamping an end cap of the chromatography cartridge of FIG. 12.
Figure 14A:
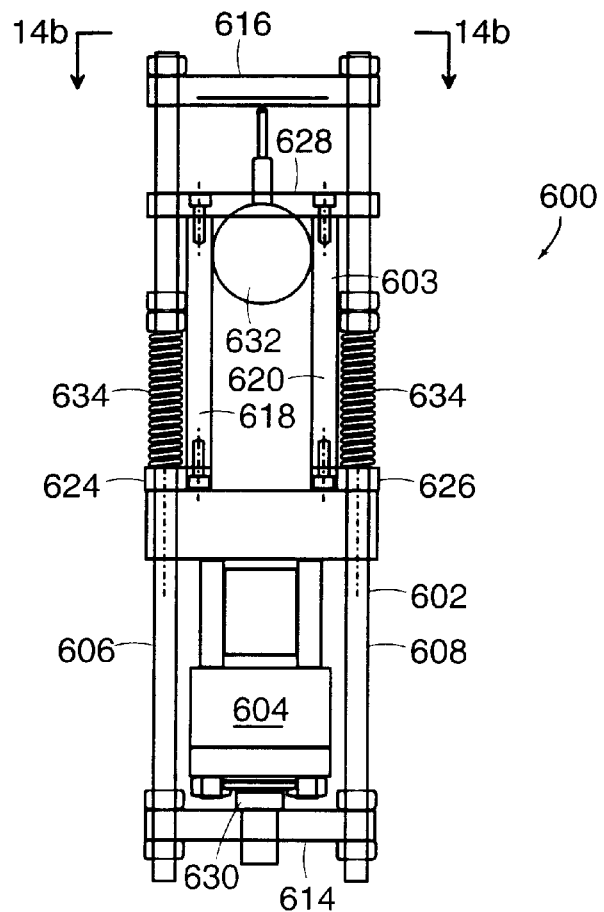

Referring to FIGS. 14a and 14b, a compressive force device 600 is used to apply the axial load to compressing ring 580. Compressive force device 600 includes a stationary frame 602 and a movable frame 603. Frame 602 includes four stationary, vertical struts 606, 608, 610 and 612 and lower and upper stationary plates 614 and 616, respectively. Movable frame 603 is slidably mounted to frame 602. Movable frame 603 includes two vertical plates 618, 620, lower horizontal struts 624, 626, and upper plate 628. A hydraulic cylinder 604 is mounted between lower stationary plate 614 and lower movable struts 624, 626. When hydraulic fluid is pumped into cylinder 604, a piston rod 630 of cylinder 604 extends. This acts to lift movable frame 603, forcing plate 628 closer to plate 616. A dial indicator 632 mounted to plate 628 measures the distance between plate 628 and plate 616. Four springs 634 (two of the four springs are shown in FIG. 14a) act to lower movable frame 603 when hydraulic pressure is removed. Plates 616 and 628 define cutouts 636 which permit compressive force device 600 to be positioned about cartridge 422.

Referring again to FIG. 13a, in use, backup ring 530 is positioned in counter-bore 542 of support tube 540. Ring 520 is slid over cartridge wall 480 and up against backup ring 530. Compressing ring 580 is then side over cartridge wall 480 and onto ring 520. Compressing ring 580 preferably has a thin film of high pressure grease on inner conical wall 582. Support tube 540 is then rotated to move ring 520 until ring 520 is at the appropriate position relative to end cap 440. On clear or translucent flexible tubes, the ring may be positioned by sight. On opaque tubes, an external indicator, not shown, can be used to position the ring, or the packing mechanism which positions the unitary end can be used.

Figure 15:
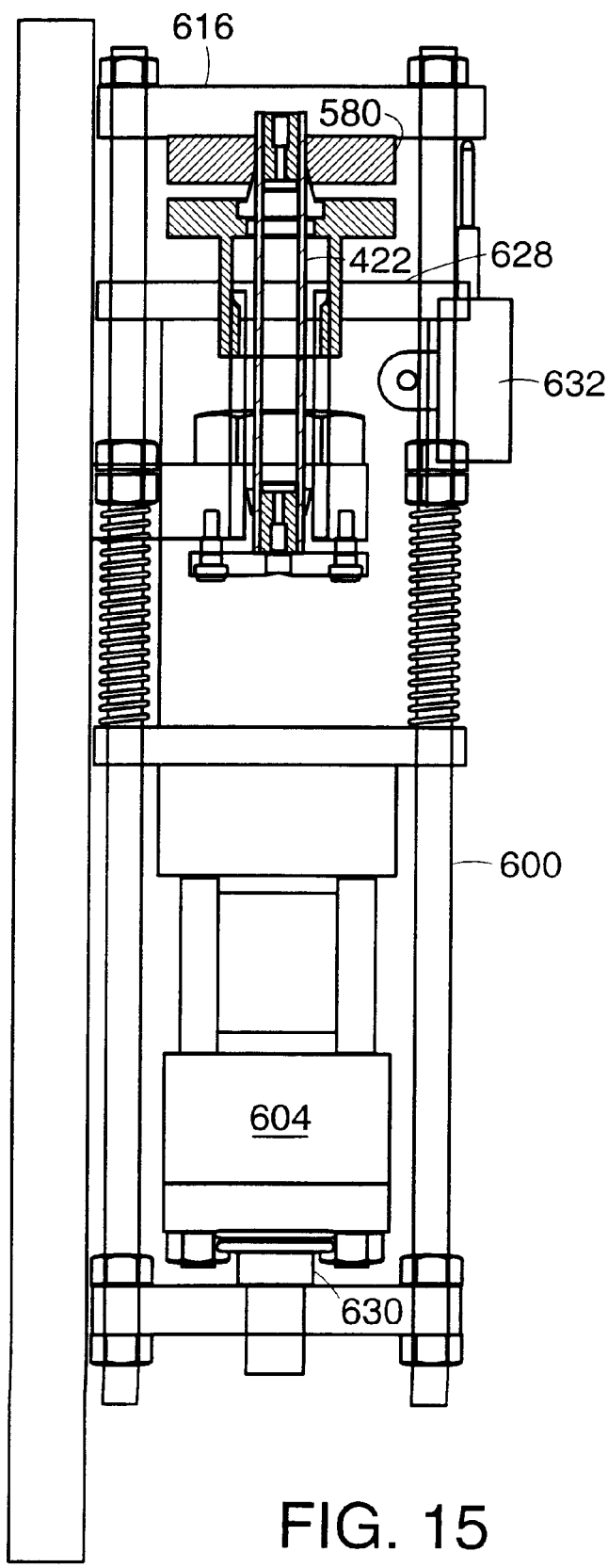
FIGS. 15 and 16 show various stages in the clamping process.
Figure 16:
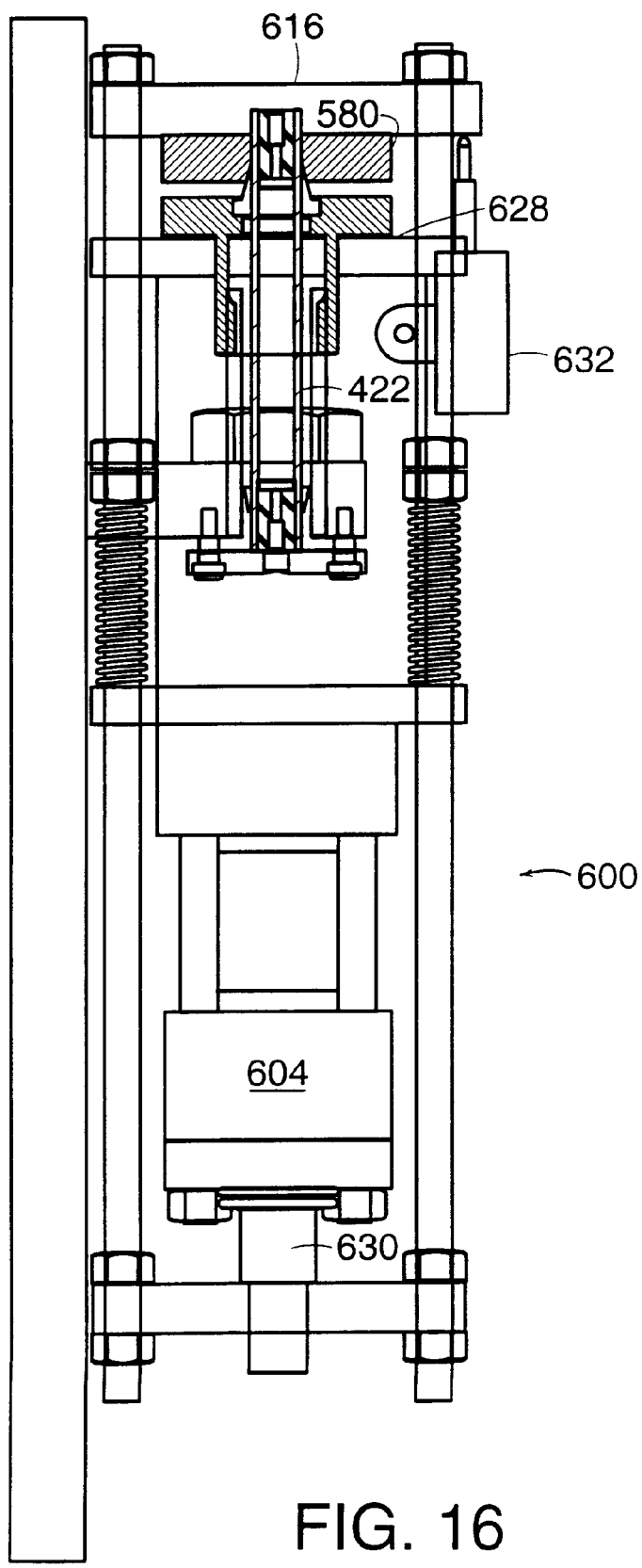

Referring to FIG. 15, compressive force device 600 is then positioned about cartridge 422 and is supported by compressing ring 580. Hydraulic fluid is pumped into cylinder 604 to extend piston rod 630 (FIG. 16). This raises plate 628 toward plate 616, applying a load to ring 520. Hydraulic pressure is increased to about 1,000 psi to remove all slop and clearances from the system. Dial indicator 632 is then set to zero. Hydraulic pressure is increased until the desired deformation of ring 520 is achieved, e.g., when the dial indicator reads 0.070". The axial deformation of 0.070" corresponds to a radial compression of about 0.034".

Hydraulic pressure is then removed, and compressive force device 600, compressing ring 580, and cartridge 422 removed. The two halves of backup ring 530 will come off cartridge 422 when pulled out of counter-bore 542 of support tube 540.

The load required to deform ring 520 depends upon the size of ring 510. For example, for a ring 520 with an inner diameter of 0.645", an outer diameter which slopes from 0.725" to 0.875" at an angle of 14°, and a length of 0.3", formed from 316 stainless steel, when the axial load applied to ring 520 reaches about 5300 pounds the yield point of the stainless steel is reached.

Ring 520 can be used in place of band clamp 244 of FIG. 8.

Other embodiments of the invention are within the scope of the following claims.

What is claimed is:

1. A chromatography cartridge assembly comprising:
    a cartridge including a wall defining a chamber for containing chromatography media, and a first end cap receiving opening,
    a first end cap received within said first end cap receiving opening, said first end cap defining a passage for flow of process fluid, and
    a clamp circumferentially located about said cartridge wall for applying a radial load through said wall to said end cap to fix said end cap in a desired position, said clamp including a conical member.

2. The chromatography cartridge assembly of claim 1 wherein said cartridge further defines a second end cap receiving opening, said assembly further comprising
    a second end cap positioned within said second end cap receiving opening, said second end cap defining a passage for flow of process fluid.

3. The chromatography cartridge assembly of claim 2 further comprising a clamp circumferentially located about said cartridge wall for applying a radial load to said second end cap to fix said second end cap in a desired position.

4. The chromatography cartridge assembly of claim 2 wherein said second end cap includes a sieve for retaining the chromatography media in said chamber.

5. The chromatography cartridge assembly of claim 4 wherein said second end cap sieve comprises a fine mesh and a course mesh.

6. The chromatography cartridge assembly of claim 2 further comprising a flexible seal located between said second end cap and said wall of said cartridge.

7. The chromatography cartridge assembly of claim 2 wherein said second end cap includes a connector for attachment to an outlet conduit.

8. The chromatography cartridge assembly of claim 1 wherein said first end cap includes flow distributor passages for distributing process fluid across a cross-sectional area of said chamber, and said second end cap includes flow collector passages for collecting process fluid from across a cross-sectional area of said chamber.

9. The chromatography cartridge assembly of claim 1 wherein an inner surface of said wall has a constant diameter.

10. The chromatography cartridge assembly of claim 1 wherein an inner surface of said wall defines a section of constant inner diameter for slidably receiving said first end cap.

11. The chromatography cartridge assembly of claim 1 wherein said assembly further comprises a second unitary end cap, said second end cap defining a passage for flow of process fluid, said second unitary end cap being integral with said cartridge.

12. The chromatography cartridge assembly of claim 1 wherein said first end cap includes a sieve for retaining the chromatography media in said chamber.

13. The chromatography cartridge assembly of claim 12 wherein said first end cap sieve comprises a fine mesh and a course mesh.

14. The chromatography cartridge assembly of claim 1 further comprising a flexible seal located between said first end cap and said wall of said cartridge.

15. The chromatography cartridge assembly of claim 1 wherein said first end cap includes a connector for attachment to an inlet conduit.

16. The chromatography cartridge assembly of claim 1 wherein said cartridge includes a flexible wall.

17. The chromatography cartridge assembly of claim 16 wherein said flexible wall is configured to radially compress said chromatography media.

18. The chromatography cartridge assembly of claim 1 further including chromatography media contained within said chamber.

19. The chromatography cartridge assembly of claim 18 wherein said chromatography media comprises a hydrophilic material.

20. The chromatography cartridge assembly of claim 18 wherein said chromatography media has an operating pressure rating greater than about 3 bar.

21. The chromatography cartridge assembly of claim 18 wherein said chromatography media has a particle size in the range of about 15–200 microns.

22. The chromatography cartridge assembly of claim 1 wherein said first end cap is sized to fit entirely within said cartridge.

23. A chromatography column comprising:
    a column having a flexible-wall, said column containing chromatography media,
    an end cap within said column, said end cap defining an inlet passage for flow of process fluid and flow distributor passages for distributing process fluid across a cross-sectional area of said column, and
    a clamp located around an outside of said column for fixing said end cap within said column, said clamp including a conical member.

24. The chromatography column of claim 23, wherein said clamp radially compresses said flexible wall to seal said end cap within said column.

25. The chromatography column of claim 23 wherein said end cap is sized to fit entirely within said column.

* * * * *

UNITED STATES PATENT AND TRADEMARK OFFICE
CERTIFICATE OF CORRECTION

PATENT NO. : 6,171,486 B1
DATED : January 9, 2001
INVENTOR(S) : Jeffrey R. Green et al.

It is certified that error appears in the above-identified patent and that said Letters Patent is hereby corrected as shown below:

Title page,
Item [56], References Cited, U.S. PATENT DOCUMENTS,
"5,167,810" reference, after "Vassarotti" add -- et al. --
"4,865,729" reference, "9/1989" should be -- 12/1989 --
"4,636,315" reference, after "Allen" add -- , Jr. --
"4,557,830" reference, after "Onitsuka" add -- et al. --
"4,250,035" reference, after "McDonald" add -- et al. --

Column 2,
Line 59, replace "ba" with -- be --

Column 3,
Line 16, after "FIG. 7" delete "is"

Column 10,
Line 45, replace "side" with -- slid --

Signed and Sealed this

Twenty-sixth Day of July, 2005

JON W. DUDAS
*Director of the United States Patent and Trademark Office*